(12) United States Patent
Thomas

(10) Patent No.: US 11,980,185 B2
(45) Date of Patent: May 14, 2024

(54) BIOFLAVONOID COMPOSITIONS AND THEIR USE FOR WATER PURIFICATION AND FOOD PRESERVATION

(71) Applicants: Citrox Biosciences Limited, Cambridgeshire (GB); Richard Thomas, Kimbolton (GB)

(72) Inventor: Howard Thomas, Cambridgeshire (GB)

(73) Assignee: Citrox Biosciences Limited, Cambridgeshire (GB)

(*) Notice: Subject to any disclaimer, the term of this patent is extended or adjusted under 35 U.S.C. 154(b) by 157 days.

(21) Appl. No.: 17/286,164

(22) PCT Filed: Oct. 18, 2019

(86) PCT No.: PCT/GB2019/052981
§ 371 (c)(1),
(2) Date: Apr. 16, 2021

(87) PCT Pub. No.: WO2020/079449
PCT Pub. Date: Apr. 23, 2020

(65) Prior Publication Data
US 2021/0386064 A1 Dec. 16, 2021

(30) Foreign Application Priority Data
Oct. 18, 2018 (GB) ...................... 1817003

(51) Int. Cl.
| | | |
|---|---|---|
| *A01N 43/16* | (2006.01) |
| *A01P 1/00* | (2006.01) |
| *A23L 3/3544* | (2006.01) |
| *A61K 8/04* | (2006.01) |
| *A61K 8/49* | (2006.01) |
| *A61Q 5/02* | (2006.01) |
| *A61Q 17/00* | (2006.01) |
| *A61Q 19/10* | (2006.01) |
| *C02F 1/50* | (2023.01) |

(52) U.S. Cl.
CPC ............... *A01N 43/16* (2013.01); *A01P 1/00* (2021.08); *A23L 3/3544* (2013.01); *A61K 8/042* (2013.01); *A61K 8/498* (2013.01); *A61Q 5/02* (2013.01); *A61Q 17/005* (2013.01); *A61Q 19/10* (2013.01); *C02F 1/50* (2013.01); *A23V 2002/00* (2013.01); *C02F 2303/04* (2013.01)

(58) Field of Classification Search
CPC ........ A01N 43/16; A01N 25/10; A01N 65/36; A01N 43/26; A01N 43/32; A01N 65/08; A01N 37/02; A01N 37/46; A61K 39/00; A61K 36/752; A61K 8/498; A61K 31/7048; A61K 31/728; A61K 47/12; A61K 8/362; A61K 8/365; A61K 8/416; A61K 8/602; A61K 8/676; A61K 8/735; A61K 8/9789; A61K 9/0014; A61K 9/0053; A61K 38/212; A61K 38/37; A61K 2039/55522; A61K 2300/00; A61K 31/353; A61K 38/00; A61K 39/39; A61K 8/042; A61K 2039/5158; A61K 2039/57; A61K 31/352; A61K 31/438; A61K 31/7036; A61K 38/1709; A61K 38/482; A61K 39/42; A61K 45/06; A61K 47/24; A61K 48/00; A61K 8/27; A61K 8/361; A61K 8/39; A61K 9/0024; A61K 9/06; A61K 9/107; A61K 9/7007; A61K 9/7069; A23V 2002/00; A23V 2200/224; A23V 2200/33; B65D 65/46; B65D 75/20; B65D 75/30; A01P 17/00; A01P 1/00; A01P 15/00
See application file for complete search history.

(56) References Cited

U.S. PATENT DOCUMENTS

| | | | |
|---|---|---|---|
| 5,035,882 | A | 7/1991 | Hussein |
| 2010/0317734 | A1 | 12/2010 | Folan |
| 2013/0085137 | A1* | 4/2013 | Grigorian ............... A61K 9/08 514/641 |
| 2018/0085292 | A1 | 3/2018 | Pierce |
| 2018/0110712 | A1 | 4/2018 | Ong |
| 2018/0228167 | A1 | 8/2018 | King |

FOREIGN PATENT DOCUMENTS

| | | |
|---|---|---|
| CN | 101882736 A | 11/2010 |
| CN | 102218021 B | 1/2013 |
| CN | 106261893 | 1/2017 |
| CN | 106360239 A | 2/2017 |
| CN | 106619193 | 5/2017 |
| CN | 107468584 | 12/2017 |
| EP | 2198862 | 6/2010 |

(Continued)

OTHER PUBLICATIONS

JP2005-152784 translation, "Kato". (Year: 2005).*
Desbois, et al., "Antibacterial free fatty acids: Activities, mechanisms of action and biotechnological potential", Appl. Microbial. Biotechnol, vol. 85, No. 6, Dec. 3, 2009, p. 1629-1642.
Hyldgaard, et al., The antimicrobial mechanism of action of e-poly-L-lysine, Appl. Environ. Microbial., vol. 80, No. 24, Oct. 10, 2014.
Ammar, et al., "Flavonoids as a possible preventive of dental plaque", Archives of Pharmacal Research, vol. 13, No. 2, 1990, pp. 211-213.
Ch Stratakos, Alexandros, et al. "The in vitro and ex vivo effect of Auranta 3001 in preventing Cryptosporidium hominis and Cryptosporidium parvum infection." Gut Pathogens 9 (2017): 1-10.

(Continued)

*Primary Examiner* — Audrea B Coniglio
(74) *Attorney, Agent, or Firm* — FisherBroyles, LLP; Adam K. Whiting; Adelaide K. Leitzel

(57) ABSTRACT

The present invention relates to pharmaceutical compositions and their use for preventing, eradicating or ameliorating infections. More particularly, the compositions comprise one or more flavonoids, such as naringin and neohesperidin and caprylic acid and/or polylysine. Such compositions can, for example, be employed for reducing or eliminating bacteria, fungi and other parasites from water, such as water intended for drinking or from food.

6 Claims, 2 Drawing Sheets

(56) References Cited

FOREIGN PATENT DOCUMENTS

| GB | 2505248 | | 2/2014 | | |
|---|---|---|---|---|---|
| GB | 2507108 | | 4/2014 | | |
| JP | 05310544 | | 11/1993 | | |
| JP | 2004107309 | A | 4/2004 | | |
| JP | 2005-152784 | * | 6/2005 | ............. | C02F 11/00 |
| JP | 2005152784 | | 6/2005 | | |
| KR | 20050063182 | | 6/2005 | | |
| KR | 20160007839 | | 1/2016 | | |
| KR | 20190011844 | | 2/2019 | | |
| WO | 2000011956 | | 3/2000 | | |
| WO | 2001015536 | | 3/2001 | | |
| WO | 2006117029 | A1 | 11/2006 | | |
| WO | 2008009956 | | 1/2008 | | |
| WO | 2008009958 | | 1/2008 | | |
| WO | 2010089600 | | 8/2010 | | |
| WO | WO2010/089600 | A1 * | 8/2010 | ............. | A01N 43/16 |
| WO | 2011067721 | | 6/2011 | | |
| WO | 2012017186 | A1 | 2/2012 | | |
| WO | 2014122446 | | 8/2014 | | |
| WO | WO2014/122446 | A1 * | 8/2014 | ............. | A01P 21/00 |
| WO | 2016102931 | A1 | 6/2016 | | |
| WO | 2020079450 | A1 | 4/2020 | | |

OTHER PUBLICATIONS

Najjar et al., "Natural Antimicrobials e-Poly-L-lisine and Nisin A for Control of Oral Microflora." Probiotics & Antimicrobial Proteins ( 2009) 1:143-147. (Year: 2009).

Newseed Chemical Co., Limited, "EpsilonPoly L Lysine: What is polylysine, e." https://www.foodsweeteners.com>epsilon-poly-l-lysine. Published online Feb. 21, 2018 (Year: 2018).

Putnik, et al., "Innovative "green" and novel strategies for the extraction ofbioactive added value compounds form citrus wastes—A review", Molecules, vol. 22, No. 680,2017, pp. 1-24.

Tsui, et al., "The inhibitory effects of naringin on the growth of periodontal pathogens in vitro", Phytotherapy Research, vol. 22, 2008, pp. 401-406.

Yu, et al., "Supercritical fluid extraction of liminoids and naringin from grapefruit (*Citrus paradisi* Macf.) seeds", Food Chemistry, vol. 105, 2007, pp. 1026-1103.

Yue, et al., "Influence of naringenin on the biofilm formation of *Streptococcus* mutans", Journal of Dentistry, vol. 76,2018, pp. 24-31.

* cited by examiner

BIOFLAVONOID COMPOSITIONS AND THEIR USE FOR WATER PURIFICATION AND FOOD PRESERVATION

CROSS-REFERENCE

This application is a 371 National Stage filing and claims the benefit under 35 U.S.C. § 120 to International Application No. PCT/GB2019/052981, filed 18 Oct. 2019, which claims priority to Great Britain Application No. 1817003.5, filed 18 Oct. 2018, each of which is incorporated herein by reference in its entirety.

BACKGROUND OF THE INVENTION

Various flavonoids have been suggested to possess antibacterial properties. PCT/GB2007/002756, PCT/GB2007/002758 and EP2198862 describe particularly effective compositions containing flavonoids (and which are incorporated herein by cross-reference).

One family of commercial products is available under the trade mark Citrox which have proved particularly advantageous in respect of antibacterial properties.

Nevertheless, known bioflavonoid anti-infective agents are not always as effective as could be wished when treating certain organisms in all circumstances. Thus, for example an enhancement in effectiveness is often desirable in the case of particularly difficult problems such as preventing, eradicating or ameliorating infections resulting from the presence of *Clostridium difficile* spores and methicillin resistant *Staphylococcus aureus*, or certain biofilm forming bacteria.

The present invention addresses such problems by providing compositions which comprise a bioflavonoid component and polylysine and/or caprylic acid component.

DESCRIPTION

The present invention provides a composition which comprises one or more flavonoids of Formula (I)

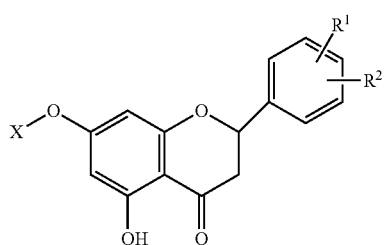

wherein $R^1$ is hydroxyl or methoxyl and $R^2$ is hydrogen, hydroxyl or methoxyl and X is hydrogen or a saccharide, and caprylic acid and/or polylysine.

Aptly in the first component $R^2$ is hydrogen and $R^1$ is in the 3- or 4-position. Alternatively, aptly in the first component $R^2$ is 3-hydroxy and $R^1$ is 4-methoxyl.

Suitably X in a compound of the Formula (I) is H.
Suitably X in a compound of Formula (I) is a saccharide.
Favourably X is a disaccharide.
Suitable disaccharides include combinations of two monosaccharide, suitably pyranoses, linked by a glycosidic bond, for example rhamnose and glucose, for example L-rhamnose and D-glucose.

Suitable disaccharides can have the structure:

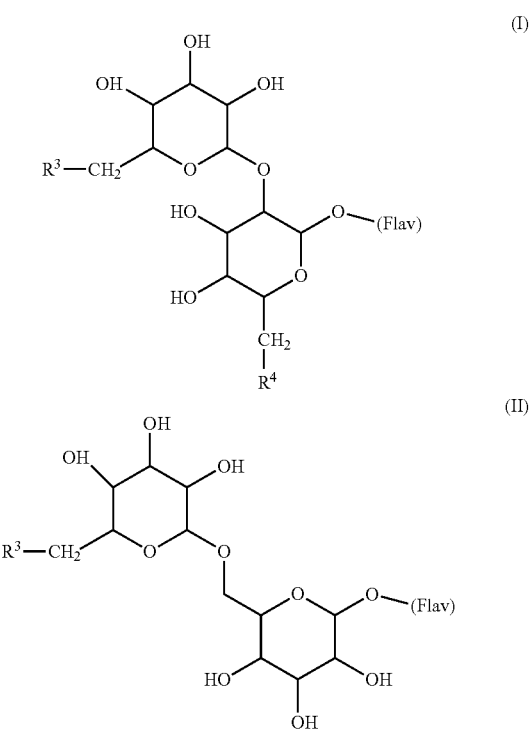

wherein one of $R^3$ and $R^4$ is H and the other OH or both are H or both are OH. Aptly $R^3$ is H and $R^4$ is OH so that the disaccharide is rutinose.

Favoured glycosyl groups of flavonoids for use in this invention are the disaccharides 6-O-(alpha-L-rhamnopyranosyl)-beta-D-glucopyranose, also known as rutinose, and 2-O-(alpha-L-rhamnopyra-nosyl)-beta-D-glucopyranose.

It is presently believed that the flavonoid of Formula I very suitably comprises naringin or neohesperidin or mixtures thereof. Mixtures of one or both of naringin and neohesperidin with for example, one, two or three other flavonoids of the Formula I are presently believed particularly favoured for use in this invention. Such mixtures can be obtained from extraction from bitter oranges.

Suitable compounds of Formula (I) include Neoeriocitrin, Isonaringin, Naringin, Hesperidin, Neohesperidin, Neodiosmin, Naringenin, Poncirin and Rhiofolin.

Favoured compositions for use include those which comprise either of naringin and neohesperidin or preferably both.

Particularly aptly the invention will contain naringin and neohesperidin and other flavonoids of the Formula (I).

The mixture of flavonoids may aptly contain neohesperidin and naringin, and one or more of isocriocrin, isonaringin, naringin, hesperidin, neohesperidin, neocliomin, naringenin, poncrin and rhiofolin. Such a mixture of flavonoids can be obtained from bitter oranges. Suitable mixtures can include 2, 3, 4, 5, 6, 7, 8, 9 or more compounds of Formula (I). Thus, a mixture comprising 2, 3, 5, 6, 7, 8 or 9 of the above named flavonoids is aptly, for example containing 3, or containing 4, or containing 5, or containing 6, or containing 7, or containing 8 or containing 9 of said flavonoids.

It is presently believed that mixtures of such flavonoids have advantages over the use of a single flavonoid. It is particularly advantageous that extract of bitter oranges may be employed without the need for isolating individual flavonoids if desired. The use of the composition generally comprising biomass that enhances solubility of the flavanoids. Generally, the flavonoids are present in mixtures with biomass by about 10% to 75%, more aptly 30% to 60%, for example 40% to 50%, preferably about 45%. The biomass comprises pectins and other sugar derived materials. Typically, about 40% of low molecular weight pectins are present in such biomass.

If it is desired to avoid biomass, other solubilising agents such as dextrins, for example cyclodextrin, may be employed if desired, but this is not presently envisaged as generally advantageous.

Aptly the mixture of flavonoids will comprise at least 25%, more suitably at least 40% and preferably at least 50% of naringin. More aptly the mixture will contain from 40% to 65% of naringin (wt/wt of flavonoids present).

Aptly the mixture of flavonoids will comprise at least 15%, more suitably at least 20% and preferably at least 25% of neohesperidin. More aptly the mixture will contain 20% to 35% of neohesperidin (wt/wt of flavonoid present).

In a favoured form the mixture of flavonoids will contain at least 75% of neohesperidin and naringin (wt/wt).

The composition will also comprise caprylic acid (octanoic acid) and/or polylysine.

For use in reducing contamination of drinking water, the composition will preferably comprise caprylic acid.

Favourably, when polylysine is employed, the amino acids in polylysine should be capable of forming charged polymers, for instance ε-polylysine is preferred to α-polylysine because the free amino acid groups may have a positive charge in non-basic media. Polylysine consists of 20-50, favourably 25-40 L-lysine residues with a molecular weight of 2400 Da to 6000 Da, favourably 3000 Da to 5000 Da.

The concentration range of polylysine, particularly ε-polylysine employed is aptly 0.01 to 1.00 wt-%, for example 0.1 to 0.75 wt-%, such as 0.25 to 0.5 wt-%.

The concentration range of the bioflavonoids employed is aptly 0.05 to 6 wt-%, for example 0.1 to 4 wt-% such as 0.2 to 3 wt-%.

A particular advantage of many compositions of the invention is that they may employ compounds of natural origin. Thus, for example, it is preferred to employ bioflavonoids obtained from bitter oranges. However, synthetically or semi-synthetically obtained compounds may be employed if desired instead of the ones directly extracted from natural sources although this tends to be less favourable in view of cost and less acceptable to those who prefer agents which are naturally derived from renewable resources.

The caprylic acid may likewise be derived from natural sources, such as coconut oil or palm oil.

The compositions of this invention show synergistic antimicrobial effectiveness between the bioflavonoids and the caprylic acid and/or polylysine.

It is presently believed that the preferred range is between 30 mg/L and 240 mg/L of polylysine and 0.06% to 4% bioflavonoids as best synergy is believed to then occur.

Aptly the composition comprises flavonoids of Formula I and polylysine.

Aptly the composition comprises flavonoids of Formula I and caprylic acid.

Aptly the composition comprises flavonoids of Formula I and caprylic acid and/or polylysine.

Preferably, the wt/wt ratio of flavonoids to polylysine or caprylic acid present is 6:1 to 1:4, for example 4:1 to 1:3, such as 3:1, 2:1, 1:1 and 1:2.

Such compositions may desirably contain a mixture of for example 65% to 75% of naringin and neohesperidin together with polylysine and/or caprylic acid (wt/wt) and other bioflavonoids.

It has been found that compositions of this invention are particularly effective in the presence of an additional component, which is one or more organic acids.

A surprisingly effective acid for use include citric acid or salicylic or lactic acid or pharmaceutically acceptable salt thereof, optionally together with a further organic acid or pharmaceutically acceptable salt.

Favourably an organic acid may be present, such as acids of up to 8 carbon atoms which are monobasic (i.e. 1 $CO_2H$ group), di-basic or tri-basic acid which optionally contain 1, 2 or 3 hydroxyl groups. Such organic acid may be one or more of citric acid, malic acid, lactic acid, tartaric acid, fumaric acid and the like.

Such compositions can provide an approximately neutral or acid pH, when used, for example pH of from 3-8, more aptly 3.5-7, for example 4-5.

In compositions containing a flavonoid of Formula I, polylysine and/or caprylic acid (and optionally a further organic acid) the weight/weight ratio of the compound(s) of Formula (I) to polylysine and/or caprylic acid or pharmaceutically acceptable salt thereof is 1300:1 to 1:10, more aptly 100:1 to 1:2, favourably 50:1 to 1:3 and preferably is 25:1 to 3:1, for example 20:1.

Such compositions may include a solubilising agent, for example a dextrin such as cyclodextrin, although use of biomass extracted from bitter oranges can avoid the need for this if required.

Compositions of the invention may be adapted for application to external surfaces including external surfaces of rooms, ambulances, hospital areas, plants or animals, or for internal administration to an animal and preferably a human.

The compositions of the invention show activity against a wide range of organisms including gram positive bacteria, gram negative bacteria, fungi, virus, protozoans and insect parasites. Particularly surprising the compositions may be employed against difficult bacteria such as methicillin resistant *Staphylococcus aureus* (MRSA), *Clostridium difficile* (C. diff) *Helicobacter pyroli* (H. py), and vancomycin resistant enterobacteria. The compositions of this invention may also be used against norovirus and other pathogens whereby transmission is by contact or air.

It is a particular advantage that the compositions are effective against spores of *Clostridium difficile* which can otherwise be particularly intransigent, and also against film forming bacteria.

The compositions may be administered systemically or locally if an animal is to be treated. Suitable animals include humans and food and companion animals such as cows, pigs, horses, chickens, sheep, goats, dogs and cats. Hence the compositions may be formulated for oral administration, topical administration, injection or the like as required by the medical practitioner. Particularly suitably such compositions are suitable for use to treat humans, especially by oral or topical administration. In these aspects of the invention, the compositions preferably employ caprylic acid in addition to the bioflavonoids.

If the composition is intended for food preservation, topical administration is apt, for example by washing, spraying or the like. In this aspect of the invention, the compositions preferably employ caprylic acid in addition to the bioflavonoids.

The compositions of the invention are also useful for use in conjunction with a further antibacterial agent.

Since the compositions of the invention are particularly effective for sterilizing surfaces, they are very suitably formulated in a composition useful for external use.

These may be in the form of solutions, gels, soaps, body wash, shampoo, dusting powders and aerially dispersible powder and liquids and the like.

Such compositions may be used to reduce the bacterial count on body surfaces, clothing and in the general environment particularly in hospitals, ambulances, nursing homes especially for the elderly or the like where it is particularly desirable to reduce the presence of bacteria such as C. diff or film forming bacteria.

Compositions suitable for washing the hands are particularly useful, for example in a hospital environment, for medical staff, patients and visitors.

Such compositions may also be employed to wash stethoscopes or other medical equipment.

The substantivity of the compositions (as opposed to rapid diminution of effectiveness of ethanol) is a considerable advantage.

Use against organisms showing resistance to the sterilizing effects of ethanol is proposed.

If external surfaces of enclosed spaces, such as ambulances, operating theatres, wards, kitchens (and even mortuaries) and so on are to be treated, it is particularly suitable to do so by "misting". In this a fine aerial dispersion of powder or microdroplets of composition are dispersed within the enclosed space. This can then offer a non-toxic alternative to the presently employed methods which often employ noxious gases. Since the compositions of the invention have such low toxicity they may be employed on patients and their visitors and associated clothing, linen and the like by "misting". Such "misting" is of use in vehicles such as ambulances which are required to be free of pathogens but likewise free of residual odors that are typically left following the use of noxious gases. This equally applies to other areas requiring treatment. Compositions used in this way may be in the form of a dispersible liquid, for example akin to the soap or shampoo or skin foaming compositions described hereinafter. These can also be used to whet the surfaces to similar ends.

A particular use includes antibacterial soaps, gels, detergents, lotions and the like for treating inter alia human skin and hair in order to reduce or eliminate undesired organisms.

Thus, it is possible by using compositions of this invention presented in such forms, to treat hands, the face and skin generally and the hair, both on the head and elsewhere. This can be employed to reduce bacterial count and so help to reduce the spread of methicillin resistant *Staphylococcus aureus, Clostridium difficile* and its spores and other bacteria. Similarly, the composition may be used to reduce microorganisms associated with acne, body odor or the like. A further benefit is that such compositions may be used to reduce viral transmission, for example for influenza virus, which can occur by hand contamination. Other virus that may be on the skin or membranes include HIV, herpes and the like which are also minimized by use of the compositions of the invention adapted for administration to the skin or membranes.

Parasite infestation may be treated with compositions of the invention. Such parasites include internal parasites such as protozoa which can lead to diseases of humans such as malaria, leishmaniasis and trypanosomiasis and various diarrhoeas. Other internal parasites that may be treated include flukes. External parasites that may be treated include lice, especially head lice, and scabies and fleas. Soaps and shampoos are favoured for such external application although solutions, lotions and gels are also particularly suitable. Composition may be analogous to those described in EP2198862, with the addition of the lysine and/or caprylic acid components.

Fungi for treatment include those responsible for dandruff, thrush, athlete's foot and the like, for example, *Candida albicans*. Conditions such as dandruff may be treated with soaps and shampoo but other formulation types named herein may also be used. Athlete's foot may also be treated with dusting powder. *Candida albicans* or other infecting agents in the vagina may be put up in the form or a pessary.

The compositions of the invention may also be adapted for use in the eye, for example for prophylaxis of treatment of conjunctivitis (red eye). Such compositions are aptly not at a pH below 5, for example may be buffered to pH 5 to 6. The composition of the invention may also be used for sterilising contact lenses or other material that comes into contact with the eye.

The compositions of the invention may also be used for the prophylaxis or treatment of dandruff or the like.

Compositions of the invention may therefore also suitably contain a pharmaceutically acceptable salt of choline such as choline chloride. This can further enhance effectiveness further against organisms such as *Clostridium difficile* and spores or *Clostridium difficile*.

Formulations may be composed of conventional carriers, as long as they are compatible with the active component of the compositions herein.

Thus soaps, shampoos, gels and the like may aptly contain surfactants. Many conventional surfactants may be employed but it appears certain effective formulations will employ non-ionic surfactants. Particularly effective non-ionic surfactants include alkyl polycyclosides and/or alkenyl polyglycosides (APGs) such as those containing up to 10 sugar residues coupled to a hydrocarbon chain. Oligomerisation of up to about 4 sugar residues can be desirable. Such surfactants are available under the trade name "Plantacare" for example from Henkel as "Plantacare 2000".

In some compositions minor amounts of typical anionic surfactants may be employed together with the non-ionic surfactant. Amphoteric surfactants may also be present, for example and preferably, with the non-ionic surfactants, for example those having secondary or tertiary amino and water solubilising anionic groups, such as sulphate, phosphate, phosphonate or carboxylate groups. Such amphoteric surfactants include those available under trade names such as Miranol (of Rhone-Poulenc) and Betaine, such as Dehyton from Henkel.

The compositions of the invention may optionally comprise thickening agents. Suitable thickening agents include polysaccharide thickeners such as xanthan gums, gellan gums, pectins, carageenans and the like. An apt thickening agent is xanthan gum such as Keltrol CG which is a high molecular weight polysaccharide produced by microbial fermentation. Viscosity may also be selected by use of an amphoteric surfactant such as a cocamido-propyl betaine or Tego Betaine F50 as a thickening as well as surfactant agent.

Due to growing fears that the use of synthetic chemical preservatives in the food industry can cause health hazards, there has been an increased demand for safe, natural food preservatives. Both Citrox (which includes the aforementioned bioflavonoids) and polylysine are natural, organic Gras-approved preservatives with activity against a range of organisms that could contaminate food and reduce shelf-life due to spoilage.

The compositions of the invention may be employed for the treatment of food stuffs to reduce or eliminate unwanted pathogens or organisms leading to reduction in storage life of food stuffs. Thus vegetable, fruits and meat may be treated, for example lettuce, tomatoes, cucumbers, peppers, cereals such as wheat and maize, fruit such as apples, grapes, pears and figs, and meats such as beef, pork, lamb, bacon and the like. Methods of treatment include washing, spraying, misting and the like.

The said combination may be included in chewing gums for treatment of bad breath or mouth ulcers and in deodorants to aid in their effectiveness.

The compositions of this invention may also be employed in order to purify water where local supplies are deemed of inadequate purity. This offers, for example, users in remote areas the possibility of improved drinking or washing water at acceptable cost without resorting to synthetic and possibly environmentally damaging antibacterial anti-infective agents.

The compositions of this invention may be used in the form of a solution or powder or gel enclosed in a dissolvable bag, pod or other dissolvable container.

WHO reports that over 2.6 billion people lack access to clean water, which I responsible for about 2.2 million deaths annually, of which 1.4 million are in children. Improving water quality can reduce the global disease burden by approximately 4%.

Pathogen contamination in freshwater environment (ground water, rivers and lakes and reservoirs) includes Salmonella, E. coli, S. faecalis, enteroviruses, shigellos, Bacillus megaterium, Staphylococcus, Pseudomonas aeruginosa, Staphylococcus aureus, fecal coliform, streptococci, Salmonella newport and fecal bacteria.

When used to prevent, eradicate or ameliorate infective organisms such as bacteria, fungi, protozoa, e.g. plasmodia, and other parasitic organisms, the compositions of this invention may be administered topically to an extended surface of the body, such as the skin, or may be administered directly into the blood, for example by injection or by absorption from the gastrointestinal tract having been administered thereto, for example by swallowing. Particular plasmodia infections which may be treated or addressed by prophylaxis include those causing malaria or leishmania. The compositions may also be employed where the causative organism is a trypanosomal parasite such as Trypanosoma brucei. Particular plasmodia which may be countered include Plasmodium falciparum and Plasmodium chabaudi, especially chloroquine-resistant strains.

When used ex-vivo, compositions of the invention were found to reduce malaria parasite levels by 50%, even at a dilution of 1:6000. Several strains of parasite are killed, including P. falciparum, which is often fatal, including strains resistant to chloroquine.

When using the compositions continuously for 76 hours, no schizonts are formed and no ring stages form new cycles of infection. The combination of the Citrox and polylysine and/or octanoic acid halts the life-cycle of the parasite. The use of the combination therefore disrupts the malaria parasite inside the human red blood cell.

Withdrawal of the test compounds in vitro did not result in resurgence of parasitaemia, indicating that the result is not due only to immune-protection. At 48 hours post-withdrawal, untreated controls increased six-fold, whereas treated samples showed no significant levels of parasitaemia.

When treating chloroquine-sensitive Plasmodium chabaudi infection in mice at 20 to 40 days post-treatment was not different from mice treated with chloroquine from those treated with a composition of the invention (approx. zero infection).

When treating mice, no reoccurrence of infection was seen 30 days post-treatment, indicating the malaria parasite had been killed and not merely suppressed. This also occurred if treatment was withdrawn before peak parasitaemia.

When mice were infected with a very virulent strain of Plasmodium which kills within 10 days, all treated mice were still alive 16 days post-infection.

Preliminary data indicates it is possible that the compositions of the invention also enhance activation of the immune system.

Ex-vivo, the composition of the invention killed four strains of trypanosomes, including T. brucei and a strain thereof resistant to chloroquine. In a mouse model, infection was greatly reduced, with several mice completely cleared of parasites.

Ex-vivo, the compositions of the invention were found to kill leishmania parasites even at a five-fold log dilution.

No significant toxicities were observed in any in-vivo test.

EXAMPLES

Example 1

Figure 1:
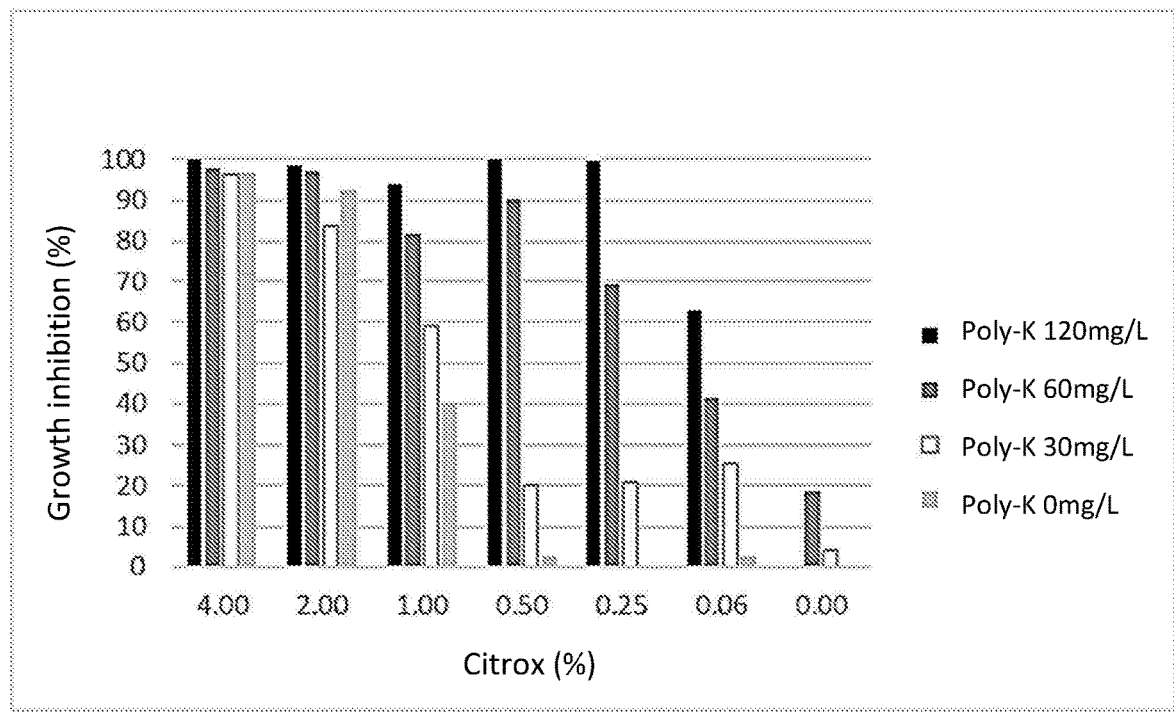
FIG. 1 shows the inhibitory effect on Escherichia coli growth of pretreatment at different concentrations of Citrox and/or ε-polylysine in a high binding microtiter plate.

A Gel Suitable as a Surgical Sanitizer

Water (481.5 g; 96.3%) was added to a beaker and stirring commenced. Keltrol CG-SFT (9.0 g; 1.8%) was added and stirring continued until dissolved. Citrox powder (2.5 g; 0.5%) was added and stirring continued until dissolved. White willow bark extract (2.0 g; 0.4%) was added and stirring continued until dissolved. Glycerol (5.0 g; 1.0%) was added and stirring continued until dissolved.

The resulting viscous gel was de-aerated. The pH was 4-5. The viscosity 7000-10000 cp at 20° C. (spindle 4/0 rpm). The pH may be adjusted with citric acid if required to bring it within the stated range.

The Willow Bark extract contains 90% of salicylic acid.

The Citrox powder (Citrox Biosciences), hereinafter Citrox, comprises 7.5% of residues of extraction from bitter oranges together with the following mixture of bioflavonoids:

| Bioflavonoid mixture | % bioflavonoid (component in biomass) |
| --- | --- |
| Neoeriocitrin | 1.1 |
| Isonaringin | 1.2 |
| Naringin | 23.4 |
| Hesperidin | 1.4 |
| Neohesperidin | 12.5 |
| Neodiosmin | 1.4 |

-continued

| Bioflavonoid mixture | % bioflavonoid (component in biomass) |
|---|---|
| Naringenin | 1.5 |
| Poncirin | 2.0 |
| Other (Rhiofolin) | 0.5 |
| Total | 45% |

Example 2

Hand Foam Composition

This may be prepared by mixing ingredients as described in Example 1.

| Salicylic acid | 0.25% |
|---|---|
| Citric acid | 0.15% |
| Bioflavonoid mixture (Example 1) | 0.0375% |
| ε-Polylysine or caprylic acid | 0.015% |
| Betaine BP20 | 1.0% |
| Glycerine | 0.5% |
| Dermosoft GMCY | 1.0% |
| Water | 97.0% |

ε-Polylysine is from Everguard PL, Impag AG.

When tested against spores of *Clostridium difficile* (NCTC 11209) according to BS EN 13704, satisfactory sporicidal activity was found with a 15 minutes contact time at 20° C.

Example 3

Sanitizing Gel

This may be prepared by mixing as described in Example 1.

| Keltrol CG-SFT | 1.7% |
|---|---|
| Bioflavonoid mixture (Example 1) | 0.0375% |
| ε-Polylysine or caprylic acid | 0.015% |
| Citric acid | 0.15% |
| Salicylic acid | 0.25% |
| Dermosoft GMCY | 1.0% |
| Glycerine | 1.0% |
| Water | 95.8% |

Such a gel provides satisfactory sporicidal activity against the spores of *C. difficile*.

Example 4

Liquid Soap

| Keltrol CG-SFT | 1.8% |
|---|---|
| Plantacare 2000 | 13.56% |
| Tego Betain F50 | 9.48% |
| Glycerine | 1.0% |
| Bioflavonoid mixture (Example 1) | 0.0375% |
| ε-Polylysine or caprylic acid | 0.015% |
| Citric acid | 0.15% |
| Salicylic acid | 0.25% |
| Dermosoft GMCY | 1.0% |
| Water | 72.66% |

Example 5

Aerially Dispersible Form

The hand foam composition of Example 2 is used in a commercial misting device to produce a mist for disinfection of surfaces.

Example 6

A commercial hand held misting device is used to direct mist at the surfaces in an ambulance and to the air space. The misting is continued until the operative is satisfied surfaces have been thoroughly treated.

The ambulance may be occupied twenty minutes after the completion of the misting.

Example 7

Immobilisation and Release of Antibacterial Activity of Citrox in Presence of ε-Polylysine High Binding plates were pre-treated with 0.1 mL of pure Citrox/ε-Polylysine solutions incubated 60' at room temperature. The concentrations of Citrox range from 0.06% to 4%. The ε-Polylysine concentrations range from 30 mg/L to 120 mg/L. The wells have been emptied and rinsed with 0.2 mL bi-distilled water. 0.2 mL of a diluted *Escherichia coli* culture (turbidity: 5 mOD at 600 nm) were given to the pre-treated wells and incubated for 3 hours at 37° C. Turbidity were measured at 600 nm and percentage of growth inhibition in comparison to untreated well calculated (FIG. 1).

Example 8

Antibacterial Activity of Citrox and ε-Polylysine Against *Escherichia coli*

The antibacterial activity of Citrox and ε-Polylysine has been tested by incubating 0.2 mL mini cultures of *Escherichia coli* (0.1 $OD_{600\ nm}$) with varying concentrations of antibacterial substances. Growth inhibition was monitored by measuring turbidity of mini cultures after 5 hours of aerobe incubation at 37° C. under agitation. Solutions were diluted to the half in cascade. The lowest concentration of the substance yielding less than 2% (6% in case of ethanol) of growth in comparison to an untreated control is considered the minimal inhibitory concentration (MIC).

Short-Term Antibacterial Activity of Citrox Toward *S. mutans* (Bactericidal Effect)

TABLE 1

| Summary of MIC (*E. coli*) extrapolated from FIG. 2 (1% corresponds to 10 g/L). Minimal inhibitory concentration (MIC) | |
|---|---|
| ε-Polylysine | 4 mg/L |
| Ampicillin | 60 mg/L |
| Ethanol | 12.5% |
| Citrox | 0.16% |
| Papaya extract | 1.25% |

The concomitant pretreatment with Citrox and ε-polylysine emphasizes the effectivity of Citrox pre-treatment. The apparent MIC of pretreating Citrox (0.25% pretreating Citrox with ε-polylysine 120 mg/L) approaches MIC of Citrox in directed exposure (0.16%).

With ε-polylysine 60 mg/L, 0.5% pretreating Citrox is required to reach inhibition, which is still significantly lower than the 2% required in absence ε-polylysine.

30 mg/L ε-polylysine corresponds to the highest concentration that does not affect significantly the antibacterial effect of Citrox pretreatment. Therefore, the preferred range of synergy is between 30 mg/L and 240 mg/L of ε-polylysine, and 0.06% to 4% of Citrox.

Example 9

Figure 3:
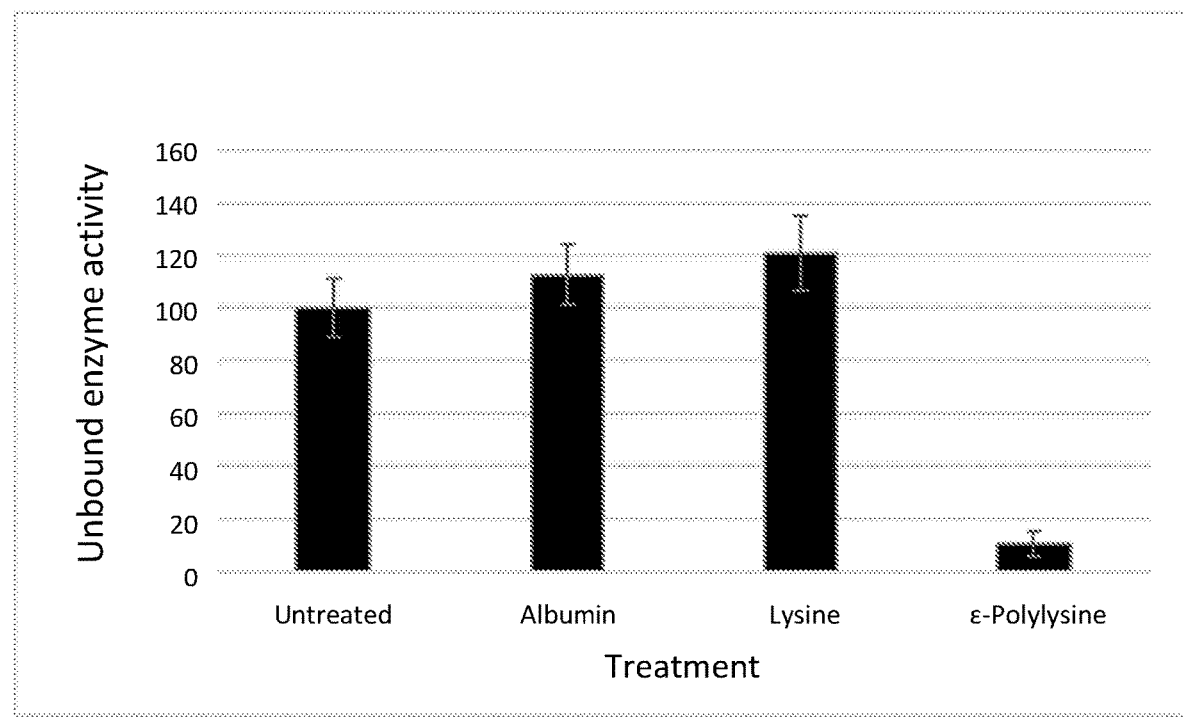
FIG. 3 shows that ε-polylysine promotes immobilization of Glucose oxidase onto silicate as assessed by measurement of residual activity in solution.

Immobilisation of Enzymatic Activity in Presence of ε-Polylysine 0.5 mg/mL glucose oxidase enzyme was incubated for 15 minutes at room temperature in an artificial saliva buffer composition including:

| | |
|---|---|
| $Na_2HPO_4$ | G/L 0.26 |
| NaCL | 6.70 |
| KSCN | 0.33 |
| KH2PO4 | 0.20 |
| KCL | 1.20 |
| NaHCO3 | 1.50, | with 2 mg/mL silicate and 0.25 mg/mL of an amino acid based compound, bovine serum albumin (BSA), lysine or ε-polylysine. The mixture was centrifuged in order to pellet the silicate and the supernatant tested for its glucose oxidase activity in presence of glucose, lactoperoxidase and a chromogen substrate (ABTS). The resulting activities were compared with the enzyme incubated with silicate in absence of an amino acid compound (FIG. 3).

Example 10

Antibacterial Activity of ε-Polylysine Against *S. mutans*

The antibacterial activity of ε-polylysine was semi-quantitatively assessed in a inhibition zone assay. 0.1 mL of a confluent *Streptococcus mutans* culture was spread over a Brain Heart Infusion (BHI) agar plate. Filter platelets (5 mm diameter) soaked with 0.01 mL substance were applied on plate. Plates were incubated 48 h at 37° C. under anaerobe conditions. The diameter of outer limit of the inhibition zones were measured, the diameter of the platelet deduced and the half result considered the radius of inhibition rings. Concentrations were tested in triplicate and their results averaged.

TABLE 2

Radius of inhibition rings around platelets diffusing the corresponding antibacterial substance across a *Streptococcus mutans* culture on agar plate.

| Antibacterial substance | Radius |
|---|---|
| ε-Polylysine 1000 mg/L | 6.5 mm |
| ε-Polylysine 100 mg/L | 2.5 mm |
| ε-Polylysine 10 mg/L | 0.5 mm |
| Ethanol | 5 mm |
| Water peroxide 0.1% | 1.5 mm |
| Water peroxide 1% | 5 mm |

When combined with Citrox the test showed significant increases in radius of inhibition zones.

Example 11

Short-Term Antibacterial Activity of Citrox Against *S. mutans* (Bactericidal Effect)

The short-term antibacterial activity of Citrox was semi-quantitatively assessed in a short exposure assay. A *S. mutans* culture, diluted in order to contain 5000 Colony Forming Units, was incubated for 10 minutes in presence of the antibacterial substance and extemporarily plated onto a BHI agar plate. Plates were incubated at 37° C. under anaerobe conditions and colony counted. Citrox at final concentrations of 5% resulted in complete absence of colony formation, as did water peroxide 0.05% under the same conditions. Citrox 0.5% reduced the count of CFU to the half (<3000 CFU).

Example 12

Assay Format Circumvents Intrinsic Antibacterial Effect of ε-Polylysine

Figure 2:
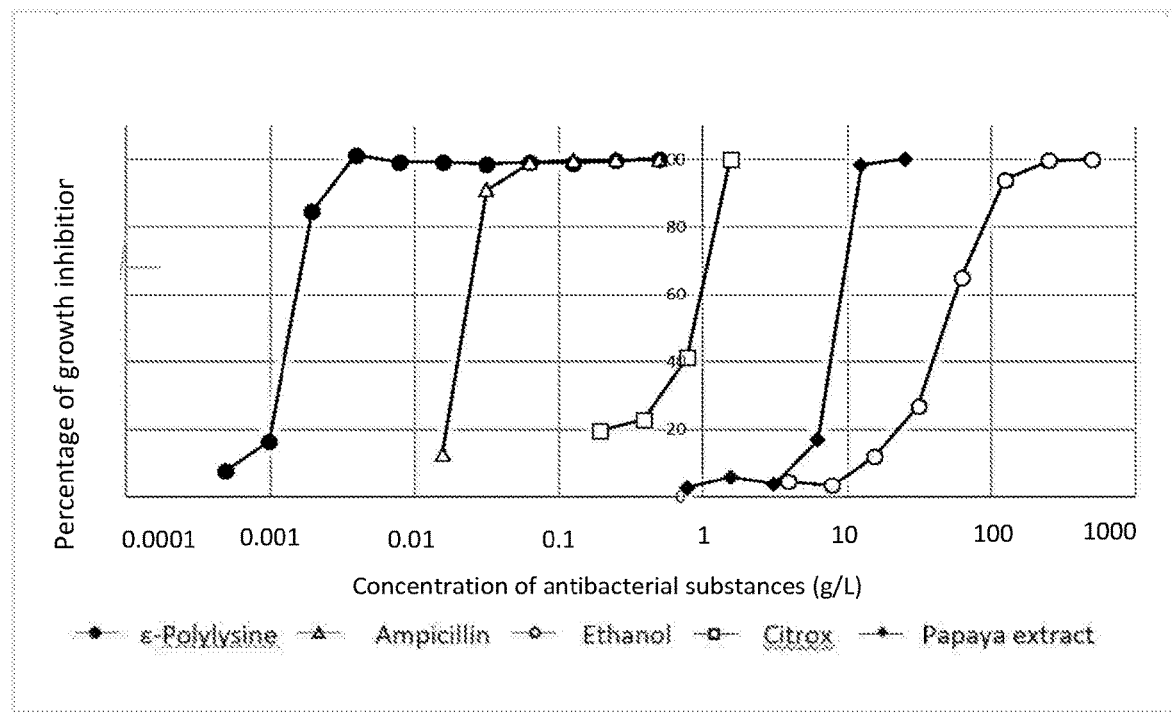
FIG. 2 shows the inhibitory effect on bacterial growth (E. coli) of direct exposure to Citrox or ε-polylysine compared to other antibacterial substances.

The experimental results show the remarkable antibacterial activities in the case of a direct exposure (in solution in a low binding plate) of ε-polylysine with a minimal inhibitory concentration (MIC) of 4 mg/L (FIG. 2 and Table 1). The pretreatment of a high binding plate with ε-polylysine does not yield any inhibitory effect despite of titers overpassing largely the MIC of direct exposure assay. This fulfils the purpose of this work that aims to circumvent the strong intrinsic antibacterial effect of ε-polylysine in order to prevent it masking the anti-bacterial effect of Citrox.

A possible explanation of the successful quenching of antibacterial effect of ε-polylysine in this format is that ε-polylysine irreversibly binds to the plate, which is a known property of the ε-polylysine. Increasing the concentration of ε-polylysine will accordingly not result in antibacterial activity, the surface being likely to be already saturated at the tested concentrations.

Since ε-polylysine strongly adsorbs onto solid surface and is not significantly released in solution, it does not affect the growth of bacteria in suspension. Although it is very likely that it prevents the surface from being colonized by bacteria, this effect concerns only the close proximity of the surface, thus a limited volume, so that it remains undetected.

Example 13

Antibacterial Effect Upon Delayed Release of Citrox is Enhanced by ε-Polylysine

The tests were performed on a plate upon which ε-polylysine strongly absorbs onto its solid surface and is not significantly released in solution. It therefore does not affect the growth of bacteria in suspension, although it prevents the surface from being colonized by bacteria.

The tests demonstrate that the antibacterial activity of Citrox is retained by the high binding plates but also allows its release in solution, thus allowing to affect the growth of the bacteria in suspension. Quantitatively, pretreating a high binding plate with Citrox 2% reaches the same inhibitory effect of a direct exposure with Citrox 0.16% (MIC Citrox).

Example 14

Tested concentrations of Citrox and ε-Polylysine employed are as follows:

| Sample No. | Citrox wt-% | Polylysine wt-% |
| --- | --- | --- |
| 1 | 4 | 0.012 |
| 2 | 4 | 0.06 |
| 3 | 4 | 0.03 |
| 4 | 4 | 0 |
| 5 | 2 | 0.012 |
| 6 | 2 | 0.06 |
| 7 | 2 | 0.03 |
| 8 | 2 | 0 |
| 9 | 1 | 0.012 |
| 10 | 1 | 0.06 |
| 11 | 1 | 0.03 |
| 12 | 1 | 0 |
| 13 | 0.5 | 0.012 |
| 14 | 0.5 | 0.06 |
| 15 | 0.5 | 0.03 |
| 16 | 0.5 | 0 |
| 17 | 0.25 | 0.012 |
| 18 | 0.25 | 0.06 |
| 19 | 0.25 | 0.03 |
| 20 | 0.25 | 0 |
| 21 | 0.06 | 0.012 |
| 22 | 0.06 | 0.06 |
| 23 | 0.06 | 0.03 |
| 24 | 0.06 | 0 |
| 25 | 0 | 0.012 |
| 26 | 0 | 0.06 |
| 27 | 0 | 0.0 |
| 28 | 0.06 | 0 |

These demonstrated that using both agents proved antibacterially more effective than the control tests employing singular composition comprising either Citrox or ε-Polylysine (sample No 4, 8, 12, 20, 24-28).

Example 15

Sterile deionised water was inoculated with a range of different microorganisms of concern in drinking water. The inoculated water was held at 20° C. overnight to allow the cells to acclimatise. The water was then treated with different concentrations of Citrox or Citrox with caprylic acid. The concentrations used were 0.05, 0.1, 0.25, 0.5 and 1.0%. The inoculated water containing the antimicrobial was held at 20° C. for three hours. The same inoculated water, without added antimicrobial, but still held at 20° C. for three hours, was used as a control. The inoculated microorganisms were enumerated after the three-hour hold time to determine the level of inactivation. The entire experiment was repeated on two separate occasions. Further details for each type of microorganism are given below.

*Escherichia coli*

Sterile deionised water was inoculated with a 5-strain cocktail of these pathogenic strains:
NCTC 9706
NCTC 9707
NCTC 11601
NCTC 11602
NCTC 11603

The strains were grown for 18 h at 37° C. in tryptone soya broth+0.6% yeast extract (TSBYE). Cells in stationary phase were harvested by centrifugation, washed in PBS and diluted in an appropriately sterile deionised water to give an initial inoculum level of approximately $10^5$-$10^6$ CFU/ml. Enumeration was by spread plating on tryptone soya agar+ 0.6% yeast extract (TSAYE), with incubation at 37° C. for 24 h.

*Enterococcus faecalis*
NCTC 8213

This strain was grown, inoculated and enumerated as described for *E. coli*.

Sulphite-Reducing Clostridia

Sterile deionised water was inoculated with a cocktail containing the following four species:
*Clostridium perfringens* ATCC 13124
*Clostridium sporogenes* NCIMB 532
*Clostridium tyrobutyricum* DSM 663
*Clostridium bifermentans* NCTC 506

Broth cultures were grown in cooked meat medium+1% glucose (steamed to remove oxygen and cooled before use) which was incubated anaerobically for 18 h at 37° C. Cells were harvested by centrifugation, washed in PBS and diluted appropriately in sterile deionised water to give an initial inoculum level of approximately $10^5$-$10^6$ CFU/ml. Enumeration was by spread plating on TSAYE, incubated anaerobically at 37° C. for 24 h.

Yeasts

Sterile deionised water was inoculated with a cocktail containing the following five species:
*Candida tropicalis* NCYC 4
*Candida solani* NCYC 2570
*Rhodotorula glutinis* NCYC 60
*Metschnikowia pulcherrima* NCYC 371
*Debaryomyces hansenii* NCYC 9

Broth cultures were grown in malt extract broth which was incubated in an orbital incubator for 72 h at 25° C. Cells were harvested by centrifugation, washed in PBS and diluted appropriately in sterile deionised water to give an initial inoculum level of approximately $10^5$-$10^6$ CFU/ml. Enumeration was by spread plating on malt extract agar, incubated aerobically at 25° C. for 72 h.

*Vibrio parahaemolyticus*

Sterile deionised water was inoculated with a cocktail containing the following four strains:
*Vibrio parahaemolyticus* NCTC 1165
*Vibrio parahaemolyticus* NCTC 1902
*Vibrio parahaemolyticus* AHPND A3
*Vibrio parahaemolyticus* AHPND D4

These strains were grown and enumerated as described for *E. coli*.

Results (Reduction in Counts after 3 hr Exposure)

The Citrox reduced counts by from 3.5 log order at 0.1% to 6.5 log orders at 1%. For the formulation also comprising caprylic acid, the reductions were increased by about 1 log order.

The Citrox reduced counts of *Enterococcus faecalis* by 4 log orders at 0.1% to 7 log orders at 1%. For the formulation also comprising caprylic acid, the reductions were increased by about 0.7 log orders.

The Citrox reduced counts of Clostridia by 2 log orders at 0.1% and 3 log orders at 1%. For the formulation also comprising caprylic acid, the reductions were increased by about 0.5 log orders.

The Citrox reduced counts of yeast by 2 log orders at 0.1% and 6 log orders at 1%. For the composition also comprising caprylic acid, the reductions were increased by about 0.5 log orders.

The Citrox reduced counts of *V. parahaemolyticus* by 1.2 log order at 0.1% and 6 log orders at 1%. The composition also comprising caprylic acid increased the reductions by 0.4 log orders at 0.1% and 0.8 log orders at 2%.

Example 16

Water was sampled from three separate locations on an urban river assumed to have a relatively high microbial load. These water samples were treated with 1% w/w Citrox and 1% w/w Citrox with caprylic acid for three hours at 20° C. The following enumerations were determined in the water with and without added antimicrobials.

Total count: yeast extract agar incubated at 37° C. for 48 h
Coliforms: VRB agar with overlay incubated at 37° C. for 24 h
*E. coli*: TBX agar incubated at 37° C. for 24 h
Sulphite-reducing Clostridia: TSC agar with overlay incubated anaerobically at 37° C. for 24 h
Enterococci: Slanetz and Bartley agar incubated at 37° C. for 4 h and then at 44° C. for 44 h Pour plating was used for all enumerations of naturally contaminated water to lower the limit of detection.

Results

Inactivation of Microorganisms in Contaminated Water

Coliforms were present at a level of 2.6 log in untreated water and were significantly reduced with Citrox and Citrox plus caprylic acid, with none detected after treatment. Results for *E. coli* were similar to coliforms, with initial counts of around 2 log reduced to below the limit of detection (1 CFU/ml) after treatment. Numbers of Enterococci were reduced from 1.6 log to below the limit of detection after treatment with both formulations.

The invention claimed is:

1. A water purification composition which comprises a mixture of flavonoids comprising naringin and neohesperidin and other flavonoids of Formula (I), comprising 40% to 65% of naringin (wt/wt of flavonoids present) and 20% to 35% of neohesperidin (wt/wt of flavonoids present)

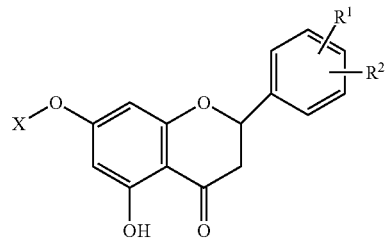

(I)

wherein $R_1$ is hydroxyl or methoxyl and $R_2$ is hydrogen, hydroxyl, methoxyl and X is hydrogen or a saccharide, and caprylic acid, for use in (ii) reducing or eliminating protozoan parasites from water, intended for drinking, or a source of water that could be contaminated.

2. The composition of claim 1 which comprises flavonoids and caprylic acid in a ratio (wt/wt) of 50:1 to 1:20.

3. The composition of claim 1 which comprises flavonoids and caprylic acid in a ratio (wt/wt) of 25:1 to 3:1.

4. The composition of claim 1 in the form of a solution or powder or gel enclosed in a dissolvable bag, pod or other dissolvable container.

5. The water purification composition of claim 1, for use in reducing the protozoan parasite concentration in water intended for drinking.

6. The composition of claim 5, wherein the concentration of a protozoan parasite selected from the group consisting of *Plasmodium, Trypanosoma,* and *Leishmania,* is reduced.

* * * * *